(12) United States Patent
Weiner et al.

(10) Patent No.: US 6,235,781 B1
(45) Date of Patent: May 22, 2001

(54) PROSTAGLANDIN PRODUCT

(75) Inventors: Alan L. Weiner, Arlington; Subhash C. Airy, Fort Worth, both of TX (US); Cody Yarborough, Fort Collins, CO (US); Julia A. Clifford, Arlington; William E. McCune, Fort Worth, both of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/487,936

(22) Filed: Jan. 20, 2000

Related U.S. Application Data

(63) Continuation-in-part of application No. 09/333,093, filed on Jun. 15, 1999.
(60) Provisional application No. 60/092,786, filed on Jul. 14, 1998.

(51) Int. Cl.$^7$ .................................................. A61K 31/215
(52) U.S. Cl. ........................... 514/530; 514/573; 514/912
(58) Field of Search .................... 514/530, 573, 514/912

(56) References Cited

U.S. PATENT DOCUMENTS

| | | | |
|---|---|---|---|
| 5,185,372 | 2/1993 | Ushio et al. | 514/552 |
| 5,340,848 | 8/1994 | Asanuma et al. | 522/157 |
| 5,516,008 | 5/1996 | Rabenau et al. | 222/153.05 |
| 5,548,007 | 8/1996 | Asanuma et al. | 524/99 |
| 5,548,008 | 8/1996 | Asanuma et al. | 524/99 |
| 5,631,287 | 5/1997 | Schneider | 514/530 |
| 5,637,367 | 6/1997 | Asanuma et al. | 428/36.92 |
| 5,856,345 | 1/1999 | Doi et al. | 514/350 |

FOREIGN PATENT DOCUMENTS

| | | |
|---|---|---|
| 0 283 151 A2 | 9/1988 | (EP) . |
| 0 770 644 A1 | 5/1997 | (EP) . |
| 63137643A2 | 6/1988 | (JP) . |
| 07112479 | 5/1995 | (JP) . |
| 07126454 | 5/1995 | (JP) . |
| 07194674 | 8/1995 | (JP) . |
| 07214648 | 8/1995 | (JP) . |
| 07304877 | 11/1995 | (JP) . |
| 09052328 | 2/1997 | (JP) . |
| WO 99/51230 | 10/1999 | (WO) . |

OTHER PUBLICATIONS

Fina® Polypropylene 3721WZ Product Information Sheet.
Rescula® Eye Drops (Package Insert and Carton).
Xalatan™ (Package Insert and Carton).
Product Labelling for Rescula® (unoprostone isopropyl ophthalmic solution, 0.15%) approved Aug. 28, 2000. Available from the FDA's Website (http://fda.gov/cder/approval/main4.htm) date = Aug. 28, 2000.

*Primary Examiner*—Zohreh Fay
(74) *Attorney, Agent, or Firm*—Patrick M. Ryan

(57) ABSTRACT

A pharmaceutical product comprising an aqueous prostaglandin formulation and a polypropylene container are disclosed. Aqueous prostaglandin formulations are more stable in polypropylene containers than polyethylene containers.

10 Claims, 4 Drawing Sheets

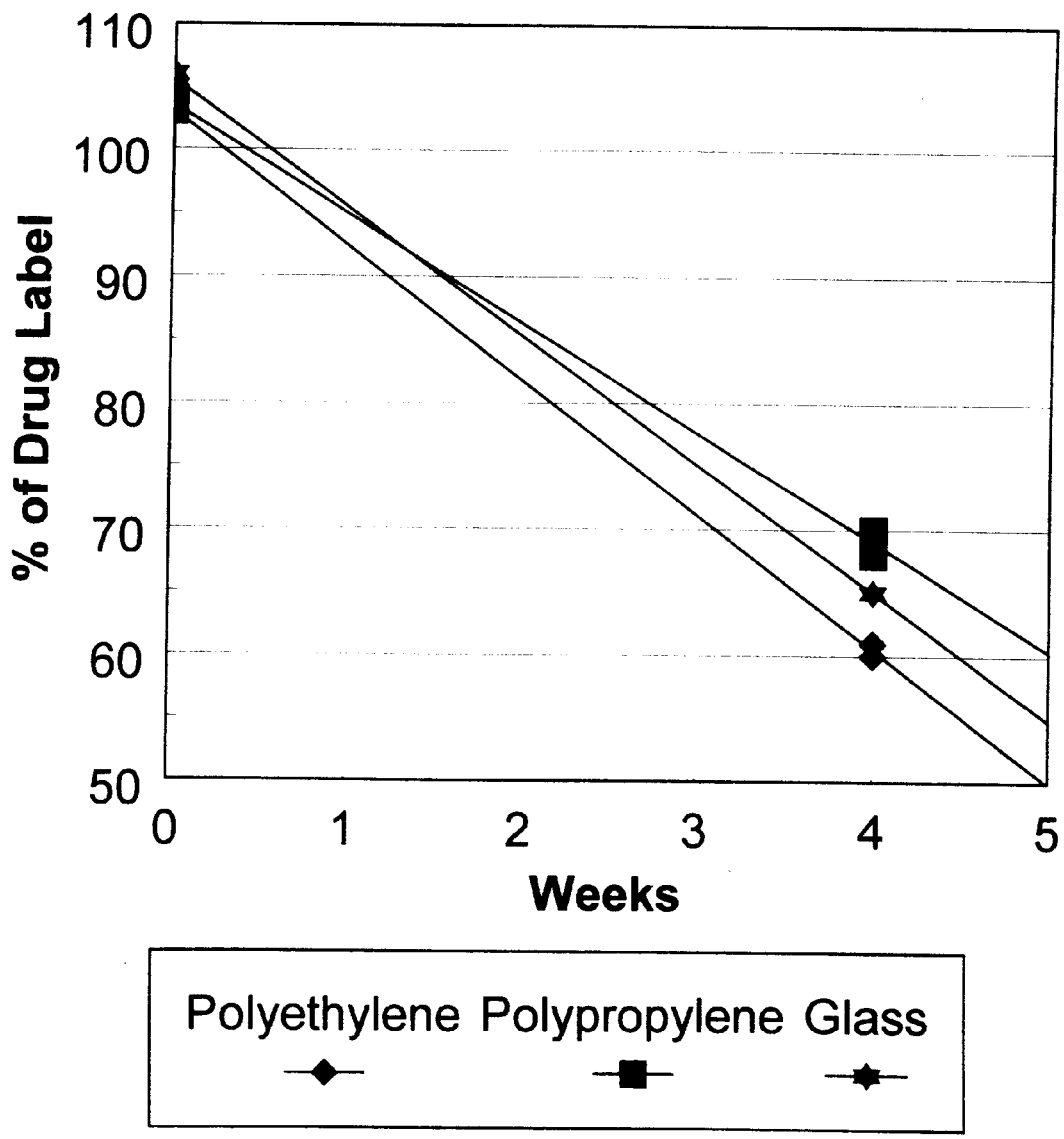

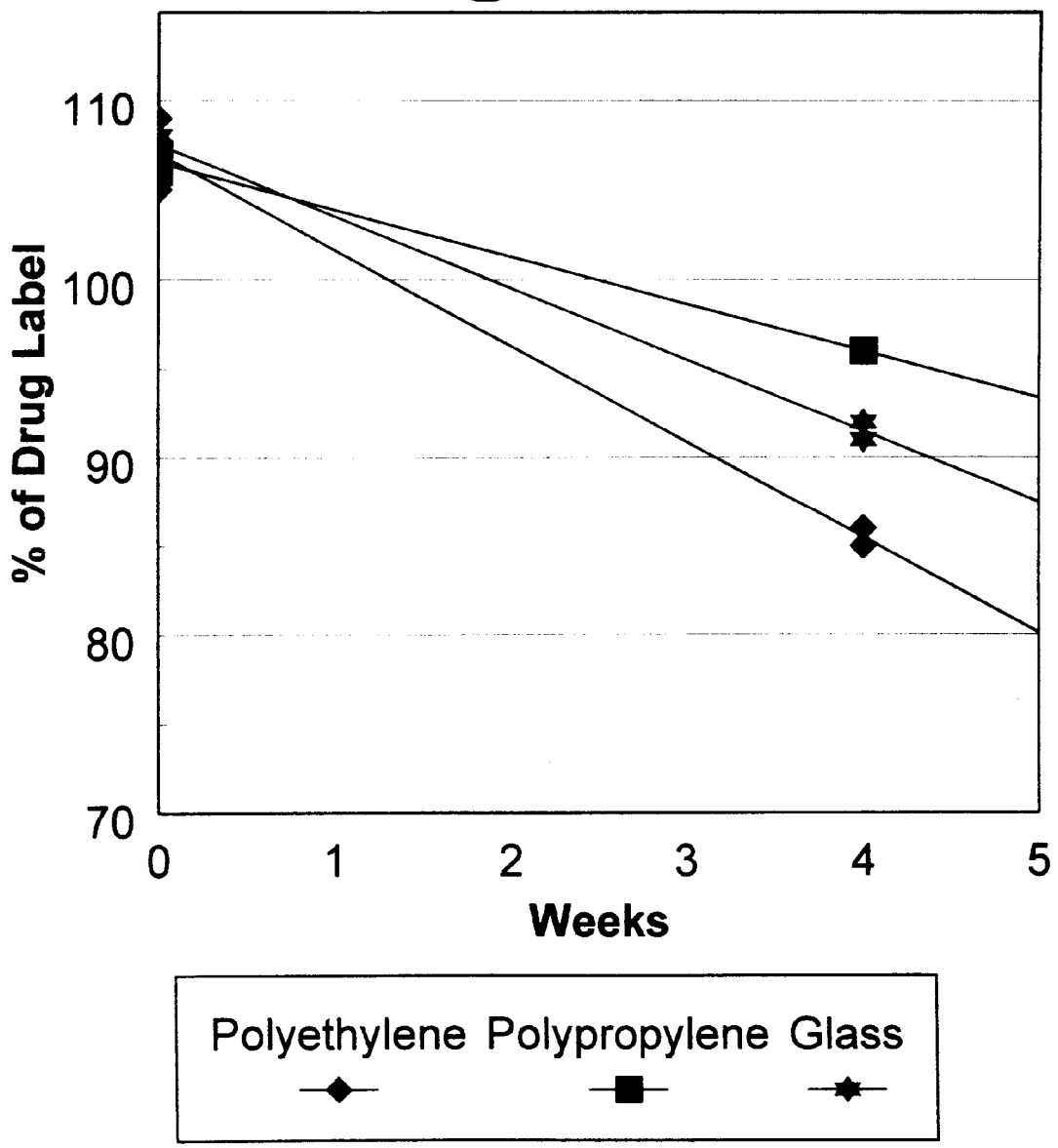

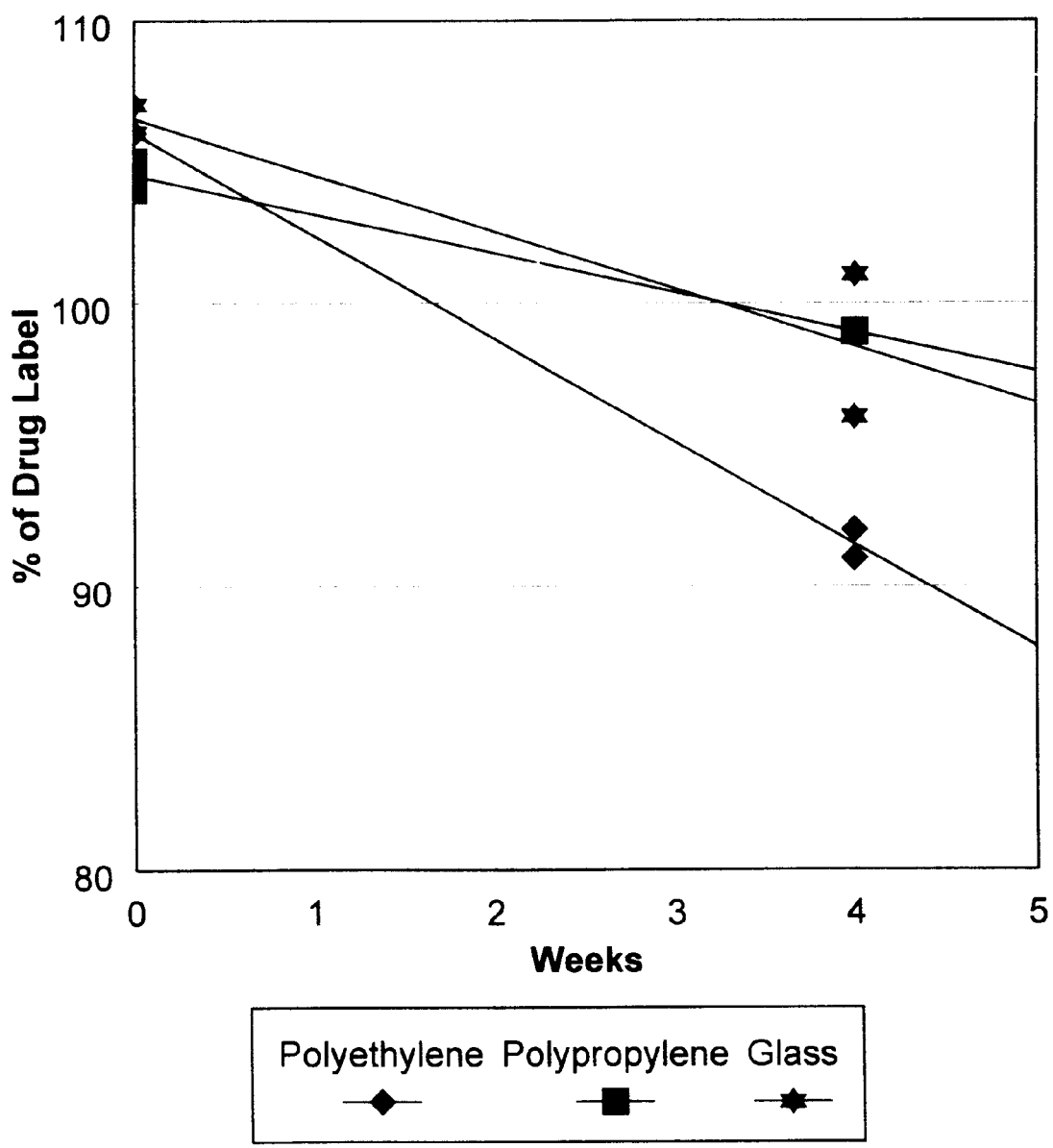

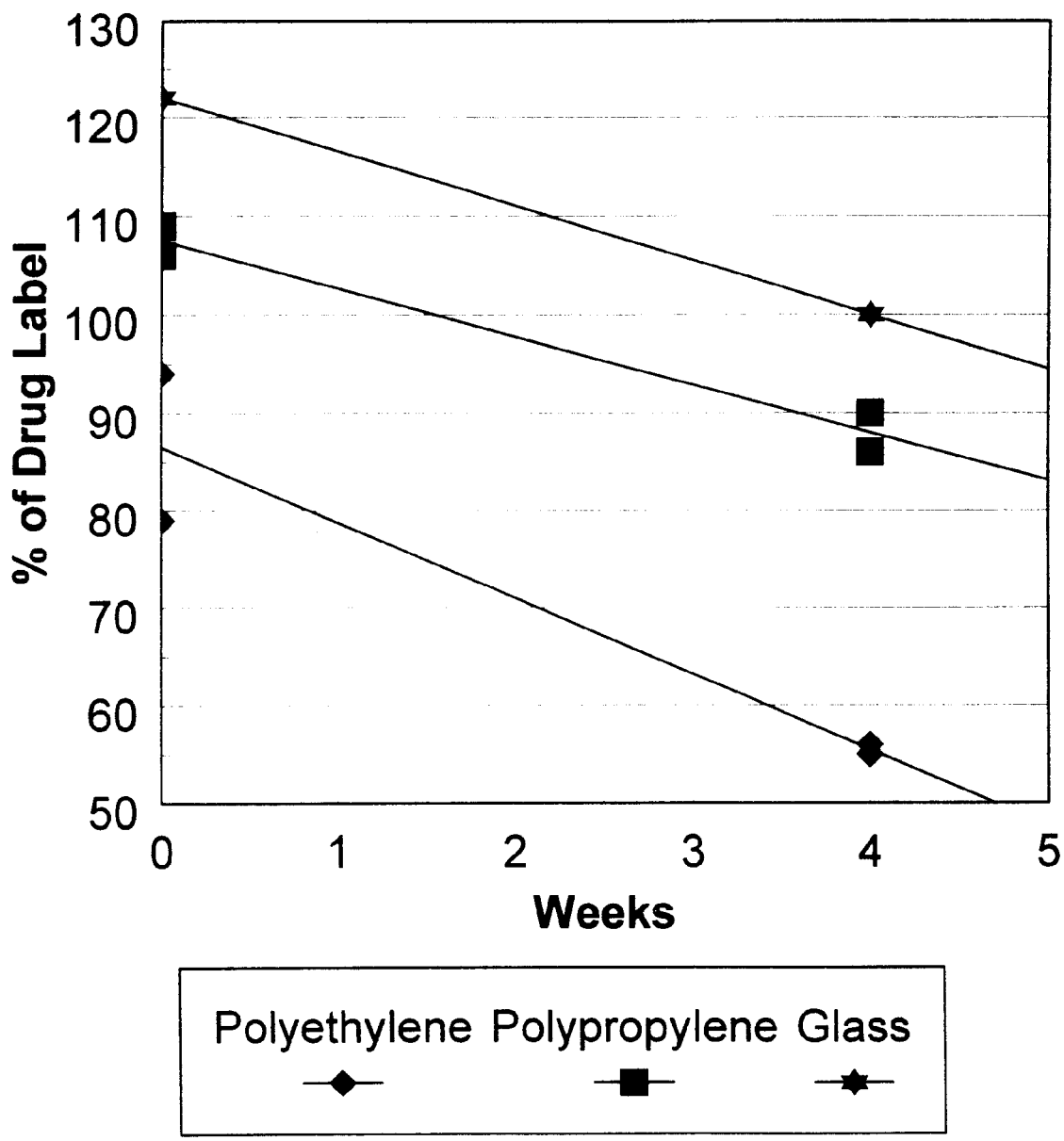

PROSTAGLANDIN PRODUCT

This application is a Continuation-in-Part of U.S. Ser. No. 09/333,093, filed Jun. 15, 1999, which claims priority from U.S. Provisional Patent Application Serial No. 60/092, 786, filed Jul. 14, 1998.

FIELD OF THE INVENTION

This invention relates to aqueous pharmaceutical compositions containing prostaglandins. In particular, the present invention relates to aqueous prostaglandin compositions packaged in polypropylene containers.

BACKGROUND OF THE INVENTION

As used herein, "LDPE" means low density polyethylene.

Prostaglandins have notoriously low water solubility, and are generally unstable. Attempts have been made to solubilize and stabilize various prostaglandins by complexing them with different cyclodextrins. See, for example: EP 330 511 A2 (Ueno et al.) and EP 435 682 A2 (Wheeler). These attempts have met with varying success.

Surfactants and/or solubilizers have been used with other types of drugs having low water solubility. However, the addition of surfactants and/or solubilizers may enhance or adversely affect the chemical stability of drug compounds. See *Surfactant Systems, Their Chemistry, Pharmacy, and Biology*, (eds. Attwood et al.), Chapman and Hall, New York, 1983, Ch. 11, particularly pp. 698–714.

The use of non-ionic surfactants, such as polyethoxylated castor oils, as solubilizing agents is known. See, for example, U.S. Pat. No. 4,960,799 (Nagy).

The use of non-ionic surfactants such as polyethoxylated castor oils in stable emulsions is also known. U.S. Pat. No. 4,075,333 (Josse) discloses stable, intravenous emulsion formulations of vitamins. El-Sayed et al., Int. *J. Pharm.*, 13:303–12 (1983) discloses stable oil-in-water emulsions of an antineoplastic drug. U.S. Pat. No. 5,185,372 (Ushio et al.) discloses topically administrable ophthalmic formulations of vitamin A which are stable preparations in which a non-ionic surfactant is used to form an emulsion of vitamin A in an aqueous medium.

U.S. Pat. No. 5,631,287 (Schneider) discloses storage-stable prostaglandin compositions containing a chemically stabilizing amount of a polyethoxylated castor oil.

Presently, there are only two commercially available ophthalmic multidose prostaglandin products, Xalatan™ (latanoprost solution; Upjohn) and Rescula™ (isopropyl unoprostone; Fujisawa). Xalatan™ is packed in a polyethylene (LDPE) container. According to the package insert, this product must be stored under refrigeration at 2–80° C. until opened. Once opened, the container may be stored at room temperature up to 25° C. for six weeks.

Rescula™ is also packaged in a polyethylene (LDPE) container.

SUMMARY OF THE INVENTION

The present invention is directed to pharmaceutical products containing an aqueous prostaglandin composition packaged in polypropylene containers. Aqueous prostaglandin compositions packaged polypropylene containers are more stable than those packaged in polyethylene containers.

BRIEF DESCRIPTION OF THE DRAWINGS

FIG. 1 compares the stability of Formulation D in clear glass, low density polyethylene and isotactic polypropylene bottles at 65° C.

FIG. 2 compares the stability of Formulation E in clear glass, low density polyethylene and isotactic polypropylene bottles at 65° C.

FIG. 3 compares the stability of Formulation F in clear glass, low density polyethylene and isotactic polypropylene bottles at 65° C.

FIG. 4 compares the stability of Formulation G in clear glass, low density polyethylene and isotactic polypropylene bottles at 65° C.

DETAILED DESCRIPTION

As used herein, "aqueous prostaglandin compositions" means aqueous compositions containing at least one prostaglandin and a major amount of water, wherein water makes up the continuous phase of the composition.

As used herein, "polypropylene" means polypropylene, substantially free (e.g., less than about 5 wt. %) of non-polypropylene olefins. The term polypropylene includes, for example, isotactic polypropylene, syndiotactic polypropylene and blends of isotactic and syndiotactic polypropylene.

The terms "prostaglandin" and "PG" are generally used to describe a class of compounds which are analogues and derivatives of prostanoic acid (1). PG's may be further classified, for example, according to their 5-membered ring structure, using a letter designation; PG's of A-J series are known. PG's may be further classified based on the number of unsaturated bonds on the side chain, e.g., $PG_1$'s (13,14-unsaturated), $PG_2$'s (13,14- and 5,6-unsaturated), and $PG_3$'s (13,14-,5,6- and 17,18-unsaturated). See U.S. Pat. No. 5,631,287, the entire contents of which are hereby incorporated by reference.

The prostaglandins which may be utilized in the present invention include all pharmaceutically acceptable prostaglandins, their derivatives and analogues, and their pharmaceutically acceptable esters and salts. Such prostaglandins include the natural compounds: $PGE_1$, $PGE_2$, $PGE_3$, $PGF_{1\alpha}$, $PGF_{2\alpha}$, $PGF_{3\alpha}$, $PGD_2$ and $PGI_2$ (prostacyclin), as well as analogues and derivatives of these compounds which have similar biological activities of either greater or lesser potencies. Analogues of the natural prostaglandins include but are not limited to: alkyl substitutions (e.g., 15-methyl or 16,16-dimethyl), which confer enhanced or sustained potency by reducing biological metabolism or alter selectivity of action; saturation (e.g., 13,14-dihydro) or unsaturation (e.g., 2,3-didehydro, 13,14-didehydro), which confer sustained potency by reducing biological metabolism or alter selectivity of action; deletions or replacements (e.g., 11-deoxy, 9-deoxo-9-methylene), chloro (or halogen) for oxygen (e.g., 9β-chloro), oxygen for carbon (e.g., 3-oxa), lower alkyl for oxygen (e.g., 9-methyl), hydrogen for oxygen (e.g., 1-$CH_2OH$,1-$CH_2OAcyl$) which enhance chemical stability and/or selectivity of action; and ω-chain modifications (e.g., 18,19,20-trinor-17-phenyl, 17,18,19,20-tetranor-16-phenoxy), which enhance selectivity of action and reduce biological metabolism. Derivatives of these prostaglandins include all pharmaceutically acceptable salts and esters, which may be attached to the 1-carboxyl group or any of the hydroxyl groups of the prostaglandin by use of the corresponding alcohol or organic acid reagent, as appropriate. It should be understood that the terms "analogues" and "derivatives" include compounds that exhibit functional and physical responses similar to those of prostaglandins per se.

Specific examples of prostaglandins suitable for use in the products of the present invention include the following compounds:

Compound No.

1. (5Z)-(9R,11R,15R)-9-chloro-15-cyclohexyl-11,15-dihydroxy-3-oxa-16,17,18,19,20-pentanor-5-prostenoic acid;
2. (5Z)-(9R,11R,15R)-9-chloro-15-cyclohexyl-11,15-dihydroxy-3-oxa-16,17,18,19,20-pentanor-5-prostenoic acid isopropyl ester;
3. (5Z)-(9R,11R,15R)-9-chloro-15-cyclohexyl-11,15-dihydroxy-3-oxa-16,17,18,19,20-pentanor-5-prostenoic acid t-butyl ester;
4. (5Z)-(9S,11R,15R)-15-cyclohexyl-3-oxa-9,11,15-trihydroxy-16,17,18,19,20-pentanor-5-prostenoic acid isopropyl ester;
5. (5Z)-(9R,11R,15S)-9-chloro-15-cyclohexyl-11,15-dihydroxy-3-oxa-16,17,18,19,20-pentanor-5-prostenoic acid isopropyl ester;
6. (5Z)-(9R,11R,15R)-9-chloro-15-cyclohexyl-11,15-dihydroxy-3-oxa-16,17,18,19,20-pentanor-5-prostenoic acid amide;
7. (5Z)-(9R,11R,15R)-9-chloro-15-cyclohexyl-11,15-dihydroxy-3-oxa-16,17,18,19,20-pentanor-5-prostenoic acid N,N-dimethylamide;
8. (5Z)-(9R,11R,15R)-9-chloro-15-cyclohexyl-11,15-dihydroxy-3-oxa-16,17,18,19,20-pentanor-5-prostenoic acid 1-methylcyclohexyl ester;
9. (5Z)-(9R,11R,15R)-9-chloro-15-cyclohexyl-11,15-dihydroxy-3-oxa-16,17,18,19,20-pentanor-5-prostenoic acid 1-methylcyclopentyl ester;
10. (5Z)-(9R,11R,15R)-9-chloro-15-cyclohexyl-11,15-dihydroxy-3-oxa-16,17,18,19,20-pentanor-5-prostenoic acid cyclopentyl ester;
11. (5Z)-(9R,11R,15R)-9-chloro-15-cyclohexyl-11,15-dihydroxy-3-oxa-16,17,18,19,20-pentanor-5-prostenoic acid 2,2-dimethylpropyl ester;
12. (5Z)-(9R,11R,15R)-9-chloro-15-cyclohexyl-11,15-dihydroxy-3-oxa-16,17,18,19,20-pentanor-5-prostenoic acid adamantyl ester;
13. (5Z)-(9R,11R,15R)-9-chloro-15-cyclohexyl-11,15-dihydroxy-3-oxa-16,17,18,19,20-pentanor-5-prostenoic acid 2,6-diisopropylphenyl ester;
14. (5Z)-(9R,11R,15R)-9-chloro-15-cyclohexyl-11,15-dihydroxy-3-oxa-16,17,18,19,20-pentanor-5-prostenoic acid 2,6-dimethylphenyl ester;
15. (5Z,13E)-(9S,11R,15R)-3-oxa-9,11,15-trihydroxy-16-(3-chlorophenoxy)-17,18,19,20-tetranor-5,13-prostadienoic acid isopropyl ester;
16. (5Z)-(9R,11R,15R)-9-chloro-15-cyclohexyl-11-hydroxy-15-methoxy-3-oxa-16,17,18,19,20-pentanor-5-prostenoic acid t-butyl ester;
17. (5Z)-(9R,11R,15R)-15-cyclohexyl-3-oxa-9,11,15-trihydroxy-16,17,18,19,20-pentanor-5-prostenoic acid isopropyl ester;
18. (5E)-(9R,11R,15R)-9-chloro-15-cyclohexyl-11,15-dihydroxy-3-oxa-16,17,18,19,20-pentanor-5-prostenoic acid isopropyl ester;
19. (5Z)-(9R,11R)-9-chloro-15-cyclohexyl-11-hydroxy-3-oxa-15-oxo-16,17,18,19,20-pentanor-5-prostenoic acid tertbutyl ester;
20. (5Z)-(9S,11R,15R)-3-oxa-17-phenyl-9,11,15-trihydroxy-18,19,20-trinor-5-prostenoic acid isopropyl ester;
21. (5Z)-(9R,11R,15R)-9-chloro-15-cyclohexyl-1-(dimethylamino)-3-oxa-16,17,18,19,20-pentanor-5-prostene-11,15-diol;
22. (5Z)-(9R,11R,15R)-9-chloro-15-cyclohexyl-11,15-dihydroxy-3-oxa-16,17,18,19,20-pentanor-5-prostenol;
23. (9R,11R,15R)-9-chloro-15-cyclohexyl-11-hydroxy-3-thia-16,17,18,19,20-pentanor-13-prostynoic acid;
24. Latanoprost (PhXA41);
25. Cloprostenol isopropyl ester;
26. (5Z)-(9S,11R,15R)-1-decarboxy-1-(pivaloyloxy)methyl-9,11,15-trihydroxy-16-[(3-chlorophenyl)oxy]-17,18,19,20-tetranor-5-prostenoic acid;
27. (5Z)-(9S,11R,15R)-1-decarboxy-1-(pivaloyloxy)methyl-9,11,15-trihydroxy-16-[(3-chlorophenyl)oxy]-17,18,19,20-tetranor-5,13-prostadienoic acid;
28. (5Z)-(9R,11R,15R)-9-chloro-15-cyclohexyl-11,15-dihydroxy-16,17,18,19,20-pentanor-5-prostenoic acid isopropyl ester;
29. (5Z)-(9S,11R,15S)-15-cyclohexyl-9,11,15-trihydroxy-16,17,18,19,20-pentanor-5-prostenoic acid isopropyl ester;
30. (5Z,13E)-(9S,11R,15R)-9,11,15-trihydroxy-16-(3-chlorophenoxy)-17,18,19,20-tetranor-5,13-prostadienoic acid amide;
31. $PGF_{2\alpha}$ isopropyl ester; and
32. Fluprostenol isopropyl ester.

All of the foregoing compounds are known. Preferred prostaglandins for use in the compositions of the present invention are Compounds 2 and 32 above.

The prostaglandin compositions packaged in polypropylene containers according to the present invention can be adapted for any route of administration. Compositions adapted for topical administration to the ears, nose or eyes are preferred, with compositions prepared for topical administration to the eye being most preferred.

In addition to one or more prostaglandins, the aqueous compositions of the present invention also contain at least one surfactant in order to help solubilize or disperse the prostaglandin in the composition. Surfactants also inhibit or prevent the adsorption of the prostaglandin on to the container walls. The surfactant may be any pharmaceutically acceptable surfactant, such as pharmaceutically acceptable cationic, anionic or nonionic surfactants. Examples of suitable surfactants include polyethoxylated castor oils, such as those classified as PEG-2 to PEG-200 castor oils, as well as those classified as PEG-5 to PEG-200 hydrogenated castor oils. Such polyethoxylated castor oils include those manufactured by Rhone-Poulenc (Cranbury, N.J.) under the Alkamuls® brand, those manufactured by BASF (Parsippany, N.J.) under the Cremophor® brand, and those manufactured by Nikko Chemical Co., Ltd. (Tokyo, Japan) under the Nikkol brand. Preferred polyethoxylated castor oils are those classified as PEG-15 to PEG-50 castor oils, and more preferred are PEG-30 to PEG-35 castor oils. It is most preferred to use those polyethoxylated castor oils known as Cremophor® EL and Alkamuls® EL-620. Preferred polyethoxylated hydrogenated castor oils are those classified as PEG-25 to PEG-55 hydrogenated castor oils. The most preferred polyethoxylated hydrogenated castor oil is PEG-40 hydrogenated castor oil, such as Nikkol HCO-40.

The aqueous compositions of the present invention optionally comprise other formulatory ingredients, such as antimicrobial preservatives, tonicity agents, and buffers. Many such formulatory ingredients are known. Examples of suitable antimicrobial preservatives for multi-dose topically administrable ophthalmic formulations include: benzalkonium chloride, thimerosal, chlorobutanol, methyl paraben, propyl paraben, phenylethyl alcohol, edetate disodium, sorbic acid, Polyquad® and other agents equally well known to those skilled in the art. Such preservatives, if present, will typically be employed in an amount between about 0.001 and about 1.0 wt. %. Examples of suitable agents that may be utilized to adjust the tonicity or osmolality of the formulations include sodium chloride, potassium chloride, mannitol, dextrose, glycerin and propylene glycol. Such agents, if present, will be employed in an amount between about 0.1 and about 10.0 wt. %. Examples of suitable buffering agents include acetic acid, citric acid, carbonic acid, phosphoric acid, boric acid, the pharmaceutically acceptable salts of the foregoing, and tromethamine. Such buffers, if present, will be employed in an amount between about 0.001 and about 1.0 wt. %.

The compositions of the present invention may additionally include components to provide sustained release and/or comfort. Such components include high molecular weight, anionic mucomimetic polymers and gelling polysaccharides, such as those described in U.S. Pat. No. 4,861,760 (Mazuel et al), U.S. Pat. No. 4,911,920 (Jani et al.), and in commonly assigned U.S. Ser. No. 08/108,824 (Lang et al.). The contents of these patents and patent applications relating to the polymers cited above are incorporated herein by reference.

As will be appreciated by those skilled in the art, the compositions may be formulated in various dosage forms suitable for delivery of aqueous compositions. In the preferred case of topical ophthalmic delivery, the compositions may be formulated as solutions, suspensions or emulsions, for example. Topically administrable ophthalmic compositions have a pH between 3.5 to 8.0 and an osmolality between 260 to 320 milliOsmoles per kilogram (mOsm/kg).

The preferred topically administrable aqueous compositions are preferably packaged in a "small volume" bottle. As used herein, the term "small volume" bottle shall mean a bottle of a size sufficient to hold a quantity of liquid medicine sufficient for 1–3 topical doses per day over 1–2 months, generally about 20 mL or less. For example, small volume containers include 5 mL-, 10 mL- and 15 mL-sized bottles adapted for topically administering eye drops. Small volume bottles made from syndiotactic polypropylene are easier to squeeze than those made from isotactic polypropylene, and oval bottles are easier to squeeze than round bottles. Accordingly, the aqueous compositions adapted for topical ophthalmic administration are preferably packaged in oval, syndiotactic polypropylene bottles.

The invention will be further illustrated by the following examples, which are intended to be illustrative but not limiting.

Preparation of Formulations A–G

Formulations A–G shown in Examples 1–7 below were prepared as follows. To a clean glass vessel of appropriate size was added approximately 75% of the batch volume of water. To this was sequentially added sodium acetate or tromethamine and boric acid, followed by mannitol, EDTA, benzalkonium chloride and either Cremophor® EL or HCO-40 so that there was complete dissolution of one ingredient prior to the addition of the next ingredient. Next the pH of the solution was adjusted using NaOH and/or HCl, and the water was added to bring the volume to 100%.

In a separate clean glass vessel, the appropriate quantity of prostaglandin was added, followed by the appropriate quantity of the vehicle whose preparation was described above. The vessel was then tightly capped and sonicated in an ultrasonic bath for one hour or alternatively stirred with a magnetic stir bar overnight, until the prostaglandin was completely dissolved. The resulting solution was then sterile filtered (0.2 μm filter).

EXAMPLE 1

The following topically administrable ophthalmic formulation was prepared in the manner described above.

| INGREDIENT | FORMULATION (w/v %) A |
|---|---|
| Compound No. 32 (prostaglandin) | 0.001 + 5% excess |
| Cremophor ® EL | 0.5 |
| Tromethamine | 0.12 |
| Boric Acid | 0.3 |
| Mannitol | 4.6 |
| Disodium EDTA | 0.01 |
| Benzalkonium Chloride | 0.01 + 5% excess |
| NaOH and/or HCl | q.s. to pH 7.4 |
| Purified Water | q.s. to 100% |

In order to test the compatibility of Formulation A with packaging materials, the following procedure was used. ETO-sterilized clear LDPE, gamma-sterilized clear LDPE, gamma-sterilized opaque LDPE and ETO-sterilized isotactic polypropylene bottles were cut into thin rectangular pieces (2 mm×10 mm). The isotactic polypropylene bottles were made from Rexene™ isotactic polypropylene (Huntsman Chemical, Inc., Odessa, Tex.). Approximately 0.5 g of each bottle material was transferred into separate 10-mL clear glass ampules (this amount roughly corresponds to the surface area with which a 5- mL-sized product would interact). Each glass ampule was then filled with 5 mL of Formulation A and sealed. The packaging materials were tested in this way in order to eliminate evaporation effects. The sealed ampulse were stored in an oven at 55° C. and were pulled out at the indicated times for HPLC analysis. The stability of the prostaglandin in Formulations A was evaluated using a semi-gradient HPLC method, employing a Delta-Pak™ C-18 column (150×4.6 mm), 5 μm, 100 Å connected with a Delta-Pak™ C-18 precolumn. The reference standard solution contained the prostaglandin in a water/ menthanol (70:30) solution.

| Mobile Phase A: | 1-Octanesulfonic Acid Sodium Salt (100 mM); pH = 3.7 |
|---|---|
| Mobile Phase B: | Acetonitrile / Methanol (10:1) |
| Injection Volume: | 100 μL |
| Detector: | 220 nm |
| Column Temperature: | 25° C. |
| Semi-Gradient Flow Rate: | 1.6 mL/min |

| Run Time (minutes) | Mobile Phase A Flow Rate (mL/min) | Mobile Phase B Flow Rate (mL/min) |
|---|---|---|
| 0 | 0.94 | 0.66 |
| 1 | 0.94 | 0.66 |
| 35 | 0.94 | 0.66 |
| 40 | 0.16 | 1.44 |

-continued

| | |
|---|---|
| Mobile Phase A: | 1-Octanesulfonic Acid Sodium Salt (100 mM); pH = 3.7 |
| Mobile Phase B: | Acetonitrile / Methanol (10:1) |
| Injection Volume: | 100 μL |
| Detector: | 220 nm |
| Column Temperature: | 25° C. |
| Semi-Gradient Flow Rate: | 1.6 mL/min |

| Run Time (minutes) | Mobile Phase A Flow Rate (mL/min) | Mobile Phase B Flow Rate (mL/min) |
|---|---|---|
| 45 | 0.94 | 0.66 |
| 50 | 0.94 | 0.66 |

The results of the compatibility tests are shown below in Table 1.

| INGREDIENT | FORMULATION (w/v %) B |
|---|---|
| Compound No. 32 (prostaglandin) | 0.001 + 5% excess |
| Cremophor ® EL | 0.1 |
| Tromethamine | 0.12 |
| Boric Acid | 0.3 |
| Mannitol | 4.6 |
| Disodium EDTA | 0.01 |
| Benzalkonium Chloride | 0.01 + 5% excess |
| NaOH and/or HCl | q.s. to pH 7.4 |
| Purified Water | q.s. to 100% |

TABLE 1

COMPATIBILITY OF FORMULATION A

PERCENT DRUG REMAINING (55° C.)

| TIME-POINT (weeks) | CLEAR GLASS AMPULES (NON-STERILIZED) | CLEAR LDPE BOTTLE (ETO STERILIZED) | CLEAR LDPE BOTTLE (GAMMA STERILIZED) | OPAQUE-LDPE BOTTLE (GAMMA STERILIZED) | ISOTACTIC POLYPROPYLENE (ETO STERILIZED) |
|---|---|---|---|---|---|
| INITIAL | 100.0 | 100.0 | 100.0 | 100.0 | 100.0 |
| 2 | 99.5 | 96.1 | 91.4 | 92.0 | 102.2 |
| 4 | 94.6 | 93.5 | 86.6 | 88.6 | 100.0 |
| 8 | 96.3 | 93.2 | 80.6 | 82.8 | 101.0 |
| % Change (8 Weeks − Initial) | (−)3.7% | (−)6.8% | (−)19.4% | (−)17.2% | (+)1.0% |

EXAMPLE 2

The following topically administrable ophthalmic formulation was prepared in the manner described above.

The compatibility of Formulation B with glass, LDPE and polypropylene containers was determined by monitoring the stability of the drug in the manner described above in Example 1 for Formulation A. The results are shown below in Table 2.

TABLE 2

COMPATIBILITY OF FORMULATION B

PERCENT DRUG REMAINING (55° C.)

| TIME-POINT (weeks) | CLEAR GLASS AMPULES (NON-STERILIZED) | CLEAR-LDPE BOTTLE (ETO STERILIZED) | CLEAR-LDPE BOTTLE (GAMMA STERILIZED) | OPAQUE-LDPE BOTTLE (GAMMA STERILIZED) | ISOTACTIC POLYPROPYLENE (ETO STERILIZED) |
|---|---|---|---|---|---|
| INITIAL | 100.0 | 100.0 | 100.0 | 100.0 | 100.0 |
| 2 | 97.2 | 96.2 | 89.4 | 88.4 | 96.3 |
| 4 | 96.5 | 94.5 | 84.6 | 82.9 | 97.3 |
| 8 | 96.8 | 92.7 | 79.2 | 77.9 | 97.0 |
| % Change (8 Weeks − Initial) | (−)3.2% | (−)7.3% | (−)20.8% | (−)22.1% | (−)3.0% |

EXAMPLE 3

The following topically administrable ophthalmic formulation was prepared in the manner described above.

| INGREDIENT | FORMULATION (w/v %) C |
|---|---|
| Compound No. 32 (prostaglandin) | 0.003 |
| HC0-40 | 0.5 |
| Tromethamine | 0.12 |
| Boric Acid | 0.3 |
| Mannitol | 4.6 |
| Disodium EDTA | 0.01 |
| Benzalkonium Chloride | 0.015 |
| NaOH and/or HCl | q.s. to pH 6.0 |
| Purified Water | q.s. to 100% |

The compatibility of Formulation C in non-sterilized syndiotactic polypropylene bottles, ETO-sterilized syndiotactic polypropylene bottles and isotactic polypropylene (Rexene®) bottles was determined as follows. The bottles were filled with 5 mL of sterile Formulation C, then stored in an oven at 55° C. and pulled at the indicated time points for HPLC analysis as described above. The syndiotactic polypropylene bottles were made from Finacene™ EOD 96-28 syndiotactic polypropylene (FINA Oil and Chemical Co., Dallas, Tex.). The compatibility results are shown below in Tables 3 and 4. Table 3 compares the compatibility of Formulation C in non-sterilized vs. ETO-sterilized syndiotactic polypropylene bottles. Table 4 compares the compatibility of Formulation C in non-sterilized isotactic and syndiotactic polypropylene bottles.

TABLE 3

COMPATIBILITY OF FORMULATION C IN STERILIZED VS. NON-STERILIZED POLYPROPYLENE BOTTLES

| | PERCENT DRUG REMAINING (55° C.) | |
|---|---|---|
| TIME-POINT (weeks) | SYNDIOTACTIC POLYPROPYLENE BOTTLES (NON-STERILIZED) | SYNDIOTACTIC POLYPROPYLENE BOTTLES (ETO-STERILIZED) |
| INITIAL | 100.0 | 100.0 |
| 2 | 98.6 | 99.5 |
| 4 | 97.8 | 98.7 |
| % Change (4 Weeks − Initial) | (−)2.2% | (−)1.3% |

TABLE 4

COMPATIBILITY OF FORMULATION C IN ISOTACTIC VS. SYNDIOTACTIC POLYPROPYLENE BOTTLES

| | PERCENT DRUG REMAINING (55° C.) | |
|---|---|---|
| TIME-POINT (weeks) | ISOTACTIC POLYPROPYLENE BOTTLES (NON-STERILIZED) | SYNDIOTACTIC POLYPROPYLENE BOTTLES (NON-STERILIZED) |
| INITIAL | 100.0 | 100.0 |
| 2 | 100.5 | 98.4 |
| 4 | 99.8 | 96.4 |
| 8 | 98.0 | 97.2 |
| % Change (8 Weeks − Initial) | (−)2.0% | (−)2.8% |

EXAMPLE 4

The following topically administrable ophthalmic formulation was prepared in the manner described above.

| INGREDIENT | FORMULATION (w/v %) D |
|---|---|
| Compound No. 2 (prostaglandin) | 0.012 + 5% excess |
| Cremophor ® EL | 0.5 |
| Sodium Acetate (trihydrate) | 0.07 |
| Mannitol | 4.3 |
| Disodium EDTA | 0.1 |
| Benzalkonium Chloride | 0.01 + 5% excess |
| NaOH and/or HCl | q.s. to pH 5.0 |
| Purified Water | q.s. to 100% |

The stability of the prostaglandin in Formulation D was evaluated in clear glass, ETO-sterilized LDPE, and ETO-sterilized isotactic polypropylene bottles as follows.

The bottles were filled with sterile Formulation D and stored in an oven at 65° C., then pulled at the indicated times for HPLC analysis. In this case, the HPLC data was generated using a Phenomenex 150×4.6 mm HPLC column with Spherisorb® 10 ODS(2) packing. The mobile phase was 560 mL phosphate to 440 mL acetonitrile, adjusted to a pH of about 8.5. The flow rate was 1 mL/minute, the detection was 200 nm UV, and the injection quantity was 20 mcL. The compatibility results are shown in FIG. 1.

EXAMPLE 5

The following topically administrable ophthalmic formulation was prepared in the manner described above.

| INGREDIENT | FORMULATION (w/v %) E |
|---|---|
| Compound No. 2 (prostaglandin) | 0.012 + 5% excess |
| Cremophor® EL | 1.5 |
| Sodium Acetate (trihydrate) | 0.07 |
| Mannitol | 4.3 |
| Disodium EDTA | 0.1 |
| Benzalkonium Chloride | 0.01 + 5% excess |
| NaOH and/or HCl | q.s. to pH 5.0 |
| Purified Water | q.s. to 100% |

The stability of the prostaglandin in Formulation E was evaluated in clear glass, LDPE, and isotactic polypropylene bottles at 65° C. according to the procedure described in Example 4 for Formulation D. The results are shown in FIG. 2.

EXAMPLE 6

The following topically administrable ophthalmic formulation was prepared in the manner described above.

| INGREDIENT | FORMULATION (w/v %) F |
|---|---|
| Compound No. 2 (prostaglandin) | 0.012 + 5% excess |
| Cremophor ® EL | 2.0 |
| Sodium Acetate (trihydrate) | 0.07 |
| Mannitol | 4.3 |
| Disodium EDTA | 0.1 |
| Benzalkonium Chloride | 0.01 + 5% excess |
| NaOH and/or HCl | q.s. to pH 5.0 |
| Purified Water | q.s. to 100% |

The stability of the prostaglandin in Formulation F was evaluated in clear glass, LDPE, and isotactic polypropylene bofties at 65° C. according to the procedure described in Example 4 for Formulation D. The results are shown in FIG. 3.

EXAMPLE 7

The following topically administrable ophthalmic formulation was prepared in the manner described above.

| INGREDIENT | FORMULATION (w/v %) G |
|---|---|
| Compound No. 2 (prostaglandin) | 0.012 + 5% excess |
| Cremophor ® EL | 1.0 |
| Sodium Acetate (trihydrate) | 0.07 |
| Mannitol | 4.3 |
| Disodium EDTA | 0.1 |
| Benzalkonium Chloride | 0.01 + 5% excess |
| NaOH and/or HCl | q.s. to pH 5.0 |
| Purified Water | q.s. to 100% |

The stability of the prostaglandin in Formulation G was evaluated in clear glass, LDPE, and isotactic polypropylene bottles at 65° C. according to the procedure described in Example 4 for Formulation D. The results are shown in FIG. 4.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method of increasing the stability of an aqueous prostaglandin composition comprising a prostaglandin and a pharmaceutically acceptable surfactant wherein the method comprises:

packaging the aqueous prostaglandin composition in a polypropylene container, provided that the polypropylene container is not packaged in a bag containing an iron oxide oxygen scavenger.

2. The method of claim 1 wherein the aqueous prostaglandin composition comprises a prostaglandin selected from the group consisting of (5Z)-(9R,11R,15R)-9-chloro-15-cyclohexyl-11,15-dihydroxy-3-oxa-16,17,18,19,20-pentanor-5-prostenoic acid; (5Z)-(9R,11R,15R)-9-chloro-15-cyclohexyl-11,15-dihydroxy-3-oxa-16,17,18,19,20-pentanor-5-prostenoic acid isopropyl ester; (5Z)-(9R,11R,15R)-9-chloro-15-cyclohexyl-11,15-dihydroxy-3-oxa-16,17,18,19,20-pentanor-5-prostenoic acid t-butyl ester; (5Z)-(9S,11R,15R)-15-cyclohexyl-3oxa-9,11,15-trihydroxy-16,17,18,19,20-pentanor-5-prostenoic acid isopropyl ester; (5Z)-(9R,11R,15S)-9-chloro-15-cyclohexyl-11,15-dihydroxy-3-oxa-16,17,18,19,20-pentanor-5-prostenoic acid isopropyl ester; (5Z)-(9R,11R,11R)-9-chloro-15-cyclohexyl-11,15-dihydroxy-3-oxa-16,17,18,19,20-pentanor-5-prostenoic acid amide; (5Z)-(9R,11R,15R)-9-chloro-15-cyclohexyl-11,15-dihydroxy-3-oxa-16,17,18,19,20-pentanor-5-prostenoic acid N,N-dimethylamide; (5Z)-(9R,11R,15R)-9-chloro-15-cyclohexyl-11,15-dihydroxy-3-oxa-16,17,18,19,20-pentanor-5-prostenoic acid 1-methylcyclohexyl ester; (5Z)-(9R,11R,15R)-9chloro-15-cyclohexyl-11,15-dihydroxy-3-oxa-16,17,18,19,20-pentanor-5-prostenoic acid 1-methylcyclopentyl ester; (5Z)-(9R,11R,15R)-9-chloro-15-cyclohexyl-11,15-dihydroxy-3-oxa-16,17,18,19,20-pentanor-5-prostenoic acid cyclopentyl ester; (5Z)-(9R,11R,15R)-9-chloro-15-cyclohexyl-11,15-dihydroxy-3-oxa-16,17,18,19,20-pentanor-5-prostenoic acid 2,2-dimethylpropyl ester; (5Z)-(9R,11,15R)-9-chloro-15cyclohexyl-11,15-dihydroxy-3-oxa-16,17,18,19,20-pentanor-5-prostenoic acid adamantyl ester; (5Z)-(9R,11R,15R)-9-chloro-15-cyclohexyl-11,15-dihydroxy-3-oxa-16,17,18,19,20-pentanor-5-prostenoic acid 2,6diisopropylphenyl ester; (5Z)-(9R,11R,15R)-9-chloro-15-cyclohexyl-11,15-dihydroxy-3-oxa-16,17,18,19,20-pentanor-5-prostenoic acid 2,6-dimethylphenyl ester; (5Z,13E)-(9S,11R,15R)-3-oxa-9,11,15-trihydroxy-16-(3-chlorophenoxy)-17,18,19,20-tetranor-5,13-prostadienoic acid isopropyl ester; (5Z)-(9R,11R,15R)-9-chloro-15-cyclohexyl-11-hydroxy-15-methoxy-3-oxa-16,17,18,19,20-pentanor-5-prostenoic acid t-butyl ester; (5Z)-(9R,11R,15R)-15-cyclohexyl-3-oxa-9,11,15-trihydroxy-16,17,18,19,20-pentanor-5-prostenoic acid isopropyl ester; (5E)-(9R,11R,15R)-9-chloro-15-cyclohexyl-11,15-dihydroxy-3-oxa-16,17,18,19,20-pentanor-5-prostenoic acid isopropyl ester; (5Z)-(9R,11R)-9-chloro-15-cyclohexyl-11-hydroxy-3-oxa-15-oxo-16,17,18,19,20-pentanor-5-prostenoic acid tertbutyl ester; (5Z)-(9S,11R,15R)-3-oxa-17-phenyl-9,11,15-trihydroxy-18,19,20-trinor-5-prostenoic acid isopropyl ester; (5Z)-(9R,11R,15R)-9-chloro15-cyclohexyl-1-(dimethylamino)-3-oxa-16,17,18,19,20-pentanor-5-prostene-11,15-diol; (5Z)-(9R,11R,15R)-9-chloro-15-cyclohexyl-11,15-dihydroxy-3-oxa-16,17,18,19,20-pentanor-5-prostenol; 9R,11R,15R)-9-chloro-15-cyclohexyl-11-hydroxy-3-thia-16,17.18,19,20-pentanor-13-prostynoic acid; latanoprost (PhXA41); cloprostenol isopropyl ester; (5Z)-(9S,11R,15R)-1-decarboxy-1-(pivaloyloxy)methyl-9,11,15-trihydroxy-16-[(3-chlorophenyl)oxy]-17,18,19,20-tetranor-5-prostenoic acid; (5Z)-(9S,11R,15R)-1-decarboxy-1-(pivaloyloxy)methyl-9,11,15-trihydroxy-16-[(3-chlorophenyl)oxy]-17,18,19,20-tetranor-5,13-prostadienoic acid; (5Z)-(9R,11R,15R)-9-chloro-15-cyclohexyl-11,15dihydroxy-16,17,18,19,20-pentanor-5-prostenoic acid isopropyl ester; (5Z)-(9S,11R,15S)-15-cyclohexyl-9,11,15-trihydroxy-16,17,18,19,20-pentanor-5-prostenoic acid iopropyl ester; (5Z,13E)-(9S,11R,15R)- 9,11,15-trihydroxy-16-(3-chlorophenoxy)-17,18,19,20-tetranor-5,13-prostadienoic acid amide; PGF$_2$a isopropyl ester; and fluprostenol isopropyl ester.

3. The method of claim 2 wherein the prostaglandin is selected from the group consisting of (5Z)-(9R,11R,15R)-

9-chloro-15-cyclohexyl-11,15-dihydroxy-3oxa-16,17,18,19,20-pentanor-5-prostenoic acid isopropyl ester; and fluprostenol isopropyl ester.

4. The method of claim 1 wherein the composition is adapted for topical ophthalmic administration and the surfactant comprises a polyethoxylated castor oil.

5. The method of claim 4 wherein the polyethoxylated castor oil is selected from the group consisting of PEG-2 to PEG-200 castor oils; and PEG-5 to PEG-200 hydrogenated castor oils.

6. The method of claim 1 wherein the polypropylene container is a polypropylene bottle adapted for topical delivery and wherein the polypropylene is selected from the group consisting of isotactic polypropylene, syndiotactic polypropylene and blends of isotactic and syndiotactic polypropylene.

7. The method of claim 1 wherein the aqueous prostaglandin composition is adapted for topical ophthalmic administration and the polypropylene container is a small volume bottle adapted for topical ophthalmic delivery.

8. The method of claim 7 wherein the polypropylene container is an oval, syndiatactic polypropylene bottle.

9. The method of claim 8 wherein the aqueous prostaglandin composition is a multi-dose composition comprising an ophthalmically acceptable preservative.

10. The method of claim 1 wherein the prostaglandin is isopropyl unoprostone.

* * * * *